(12) United States Patent
Birnkrant et al.

(10) Patent No.: US 10,485,404 B2
(45) Date of Patent: Nov. 26, 2019

(54) COMPACT IMAGE SENSOR MODULE AND METHOD OF ASSEMBLY FOR IMAGE SENSOR MODULES

(71) Applicant: KARL STORZ Endovision, Inc., Charlton, MA (US)

(72) Inventors: Dashiell Birnkrant, Worcester, MA (US); Gerard Vadenais, Bellingham, MA (US); Jordan He, Southbridge, MA (US); Jason Curtis, Nashua, NH (US)

(73) Assignee: KARL STORZ Endovision, Inc., Charlton, MA (US)

( * ) Notice: Subject to any disclaimer, the term of this patent is extended or adjusted under 35 U.S.C. 154(b) by 557 days.

(21) Appl. No.: 15/057,767

(22) Filed: Mar. 1, 2016

(65) Prior Publication Data

US 2017/0251913 A1    Sep. 7, 2017

(51) Int. Cl.
*A61B 1/00* (2006.01)
*A61B 1/05* (2006.01)
*H04N 5/225* (2006.01)
*H05K 1/18* (2006.01)
*H05K 1/02* (2006.01)

(52) U.S. Cl.
CPC .................................. *A61B 1/0011* (2013.01)

(58) Field of Classification Search
CPC . A61B 1/0661; A61B 1/0676; A61B 1/00112; A61B 1/00114; A61B 1/00121; A61B 1/00124; A61B 1/0011; A61B 1/00018; Y10S 600/92

USPC ....... 600/109, 110, 112, 132, 136, 139, 144, 600/145, 146, 149, 150, 160
See application file for complete search history.

(56) References Cited

U.S. PATENT DOCUMENTS

| 4,831,456 | A | | 5/1989 | Takamura | |
|---|---|---|---|---|---|
| 4,998,182 | A | | 3/1991 | Krauter et al. | |
| 5,021,888 | A | | 6/1991 | Kondou et al. | |
| 5,220,198 | A | * | 6/1993 | Tsuji | A61B 1/05 257/680 |
| 5,754,313 | A | | 5/1998 | Pelchy et al. | |
| 5,857,963 | A | * | 1/1999 | Pelchy | A61B 1/05 348/373 |
| 6,142,930 | A | * | 11/2000 | Ito | A61B 1/00096 348/76 |
| 6,313,456 | B1 | | 11/2001 | Miyashita et al. | |

(Continued)

*Primary Examiner* — Timothy J Neal
*Assistant Examiner* — William B Chou
(74) *Attorney, Agent, or Firm* — Russell D. Culbertson; Michael Joseph Loi; David N. Villalpando (57) ABSTRACT

An image sensor module includes a circuit board, image sensor, electronic component assembly, and cable assembly. The circuit board includes a center section located between two end sections. The end sections each extend away from the center section and define an interior area there between. The image sensor is secured to an outer face of the circuit board in the center section with sensor contact fingers being connected at the circuit board outer face in one or both end sections. The electronic component arrangement is mounted on an inner face of the circuit board in the center section. A number of wires of the cable assembly extend through an end gap between the circuit board end sections and are connected to the inner face of the circuit board so as to overlap with the sensor contact fingers along a module longitudinal axis.

20 Claims, 6 Drawing Sheets

(56) References Cited

U.S. PATENT DOCUMENTS

| | | | |
|---|---|---|---|
| 6,494,739 B1* | 12/2002 | Vivenzio | H01R 13/5804 |
| | | | 358/473 |
| 6,567,115 B1 | 5/2003 | Miyashita et al. | |
| 6,635,865 B1* | 10/2003 | Soltyk | H04N 1/02805 |
| | | | 250/208.1 |
| 6,945,929 B2* | 9/2005 | Ando | A61B 1/00114 |
| | | | 348/45 |
| 7,074,181 B2* | 7/2006 | Futatsugi | A61B 1/05 |
| | | | 600/110 |
| 7,166,537 B2* | 1/2007 | Jacobsen | A61B 1/05 |
| | | | 438/240 |
| 7,369,176 B2* | 5/2008 | Sonnenschein | H04N 5/2253 |
| | | | 348/374 |
| 7,714,931 B2 | 5/2010 | Singh et al. | |
| 7,773,122 B2 | 8/2010 | Irion et al. | |
| 7,868,429 B2 | 1/2011 | Chen et al. | |
| 7,893,956 B2 | 2/2011 | Ayrenschmalz | |
| RE43,281 E* | 3/2012 | Higuma | 600/109 |
| 8,189,062 B2 | 5/2012 | Irion et al. | |
| 8,216,127 B2 | 7/2012 | Zifeng et al. | |
| 8,310,533 B2* | 11/2012 | Morse | G02B 23/2469 |
| | | | 348/231.3 |
| 8,698,887 B2 | 4/2014 | Mikino et al. | |
| 8,821,382 B2 | 9/2014 | Kagawa | |
| 9,078,579 B2 | 7/2015 | Gilad et al. | |
| 9,113,845 B2 | 8/2015 | Gilad et al. | |
| 2002/0080233 A1* | 6/2002 | Irion | H04N 5/2251 |
| | | | 348/65 |
| 2005/0285973 A1 | 12/2005 | Singh et al. | |
| 2009/0152662 A1 | 6/2009 | Gilad et al. | |
| 2009/0268019 A1 | 10/2009 | Ishii et al. | |
| 2010/0326703 A1 | 12/2010 | Gilad et al. | |
| 2012/0197081 A1* | 8/2012 | Kimura | A61B 1/00124 |
| | | | 600/110 |
| 2013/0258183 A1 | 10/2013 | Kamei | |
| 2014/0009593 A1* | 1/2014 | Segi | A61B 1/005 |
| | | | 348/76 |
| 2014/0371530 A1* | 12/2014 | Wieters | A61B 1/0011 |
| | | | 600/109 |
| 2015/0297069 A1* | 10/2015 | Coppersmith | F21V 29/70 |
| | | | 600/132 |

* cited by examiner

COMPACT IMAGE SENSOR MODULE AND METHOD OF ASSEMBLY FOR IMAGE SENSOR MODULES

TECHNICAL FIELD OF THE INVENTION

The invention relates to imaging devices and particularly to image sensor modules and methods for assembling such modules.

BACKGROUND OF THE INVENTION

Imaging devices are used in many different applications in industry and medicine. For example, an endoscope is an instrument that includes an elongated thin shaft that may be inserted into a cavity to obtain an image from the cavity. Early endoscopes included a light transmission element or arrangement to transmit an image from a distal end of the shaft to an eyepiece of the instrument. Rather than transmitting the light image itself from the distal end of the shaft to an eyepiece, many modern endoscopes employ an electronic imaging device at the distal end of the shaft. The imaging device receives an image from the distal end of the shaft and converts the image to electrical signals. These electrical signals are communicated the length of the shaft to processing elements which ultimately use the signals to generate a signal for driving a display device to reproduce the image received at the distal end of the shaft.

The electronic imaging device employed by the more modern approach includes an image sensing module along with an arrangement of one or more lenses which introduce an image to the image sensing module. The image sensing module includes an image sensor and electronic components which must be located in close proximity to the image sensor. One or more printed circuit boards (referred to hereafter simply as "circuit boards"), provide mounting points for the image senor and electronic components, and also provide connecting points for wires which provide power and wires which are used to carry the electrical signals from the distal end of the shaft to the signal processing and display driving components of the endoscope.

It is desirable for the shaft of an endoscope to be readily flexible along its entire length to facilitate placement of the shaft distal end at a desired location within a cavity. However, the electronic imaging device employed in modern endoscopes is essentially a rigid element. Thus where an electronic imaging device is used, the length of the shaft which covers the imaging device does not have the desired flexibility. It is therefore desirable to reduce the overall length of the imaging device.

One way to reduce the overall length of an imaging device is to reduce the length of the image sensor module included in the device. However, the image sensor module must still include the necessary elements and provide room for the various electrical connections between elements.

SUMMARY OF THE INVENTION

The invention encompasses image sensor modules having a respective configuration that facilitates a reduction in the overall length of the module. The invention also encompasses endoscopes employing such a compact image sensor module and further encompasses methods for assembling an image sensor module to produce a compact form.

An image sensor module according to a first aspect of the invention includes a circuit board, an image sensor, an electronic component arrangement, and a cable assembly. The circuit board defines an inner face and an outer face and has a center section located between first and second end sections. The end sections are each oriented to project away from the center section, and particularly from a plane defined by the inner face in the center section. In this arrangement, the first and second end sections define an interior area there between. This interior area extends from the circuit board center section and terminates at the opposite end at an end gap between the first and second end sections. The image sensor is secured to the outer face of the circuit board in the center section, and includes a number of contact fingers extending from a lateral side of the image sensor and along the circuit board outer face in the first end section at least to a contact finger connection point. The electronic component arrangement is operatively mounted on the circuit board inner face in the center section, opposite to the image sensor. A number of wires of the cable assembly extend through the end gap and are operatively connected to the inner face of the circuit board. At least one of the cable assembly wires is connected to the inner face at a wire connection point which is closer than the contact finger connection point to the plane defined by the circuit board inner surface in the center section.

In the arrangement according to this aspect of the invention one or more wires of the cable assembly overlap with the image sensor contact fingers along a longitudinal axis of the image sensor module. This overlap facilitates a compact form for the image sensor module. In particular, the connection of the image sensor contact fingers on the circuit board outer face in an end section of the circuit board and the connection of the cable assembly wires on the circuit board inner face allows the image senor contact fingers and cable assembly wires to overlap along the longitudinal axis of the image sensor module to minimize the overall length of the image sensor module.

A second aspect of the invention includes an endoscope which incorporates an image sensor module according to the first aspect of the invention. An endoscope according to this second aspect of the invention includes an instrument body and an elongated shaft. The elongated shaft includes a proximal end operatively connected to the instrument body and a distal end in which is mounted an imaging device. An image sensor module according to the first aspect of the invention is included in this imaging device at the distal end of the shaft. The cable assembly wires for the image sensor module extend within the shaft along its length to an interior of the instrument body where they are operatively connected to components within the instrument body.

In some embodiments of an image sensor module according to the first aspect of the invention, the first and second end sections converge as they extend away from the center section. This arrangement of converging circuit board end sections produces a triangular shape that allows the imaging device in which the imaging module is incorporated to taper gradually to meet the cable assembly.

In order to accommodate the arrangement in which the circuit board end sections extend away from the circuit board center section, converging or otherwise, the circuit board for embodiments according to the first aspect of the invention may be flexible. One embodiment includes a circuit board which is flexible only in interface areas between the center section and each end section. In other embodiments the circuit board is flexible along the entire length and width thereof.

In some embodiments an image sensor module according to the first aspect of the invention includes cable assembly wires connected to two separate areas of the circuit board. In these embodiments a first portion of the cable assembly wires are connected in the first end section and a second portion of the cable assembly wires are connected in the second end section. Both the first and second portions of cable assembly wires are connected to the respective end section at the inner face of the circuit board. To help facilitate the connections at the two opposing end sections of the circuit board, the first portion of the cable assembly wires may be included in a first cable and the second portion of the cable assembly wires may be included in a second cable separate from the first cable.

In view of the placement of the electronic component arrangement on the inner face of the circuit board in the center section and the placement of the cable assembly wires in close proximity at the inner face of the circuit board, an image sensor module according to the first aspect of the invention may include dielectric shielding for the electronic component arrangement. In particular, the image sensor module may further include a dielectric shield separate from the electrical component arrangement. This dielectric shield may be positioned in the interior area between the circuit board end sections so as to separate the electric component arrangement from the cable assembly wires operatively connected at the inner face of the circuit board in the end sections.

A third aspect of the invention includes a method of assembling an image sensor module. Such a method employs a circuit board according to the above-described aspects of the invention which is flexible at least at the interface areas between the circuit board center section and each end section. Methods according to this third aspect of the invention may include attaching an image sensor to the outer face of the circuit board in the center section. This attachment to the circuit board center section places the sensor contact fingers so that they extend from at least a first lateral side of the image sensor. In addition to attaching the image sensor, the third aspect of the invention also includes soldering each of the cable assembly wires to a respective set of one or more wire soldering pads located on the circuit board inner face, that is, the face opposite to the outer face to which the image sensor is to be secured. The steps of attaching the image sensor and soldering the cable assembly wires may be performed in any order relative to each other, preferably while the circuit board remains in a planar form. Also, the circuit board may be received for the assembly method already populated with the electronic component arrangement, or the electronic component arrangement may be operatively connected to the circuit board center section inner face as part of the assembly method.

Once the image senor and cable assembly wires are connected to the circuit board and the electronic component arrangement is also operatively connected to the circuit board, methods according to this third aspect of the invention may include bending the circuit board to the image sensor module configuration described above for the first aspect of the invention. In particular, the circuit board is bent so that the first end section and the second end section are brought toward each other to a position in which the two end sections face each other and extend away from the center section.

Methods according to the present invention further include bending the sensor contact fingers toward the outer face in the respective end section so that the sensor contact fingers may be soldered in place. Once bent to the desired positions, the methods include soldering the sensor contact fingers to respective image sensor soldering pads located on the outer face in the respective end section. In this bent and soldered position, the sensor contact fingers, or at least one of them, extends to a point spaced further than at least one of the wire contact pads from a plane defined by the circuit board inner face in the center section.

As noted above in connection with the first and second aspects of the invention, the cable assembly wires may include two portions each connected to a respective one of the circuit board end sections. Thus methods according to the invention may include soldering each wire of the first portion of the wires to wire soldering pads in the first end section and soldering each wire of a second portion of the wires to wire soldering pads in the second end section. Where the different portions of cable assembly wires are each included in a separate cable, the assembly method may further include repositioning the first cable and second cable as the circuit board is bent to bring the circuit board end sections toward each other.

Methods according to the invention may also include placing a dielectric shield in a position separating the electronic component arrangement from the cable assembly wires soldered to the inner face of the circuit board in a respective end section. This dielectric shield may be positioned within the assembly preferably before bending the circuit board to the desired final assembled position.

These and other advantages and features of the invention will be apparent from the following description of illustrative embodiments, considered along with the accompanying drawings.

DESCRIPTION OF ILLUSTRATIVE EMBODIMENTS

Figure 1:
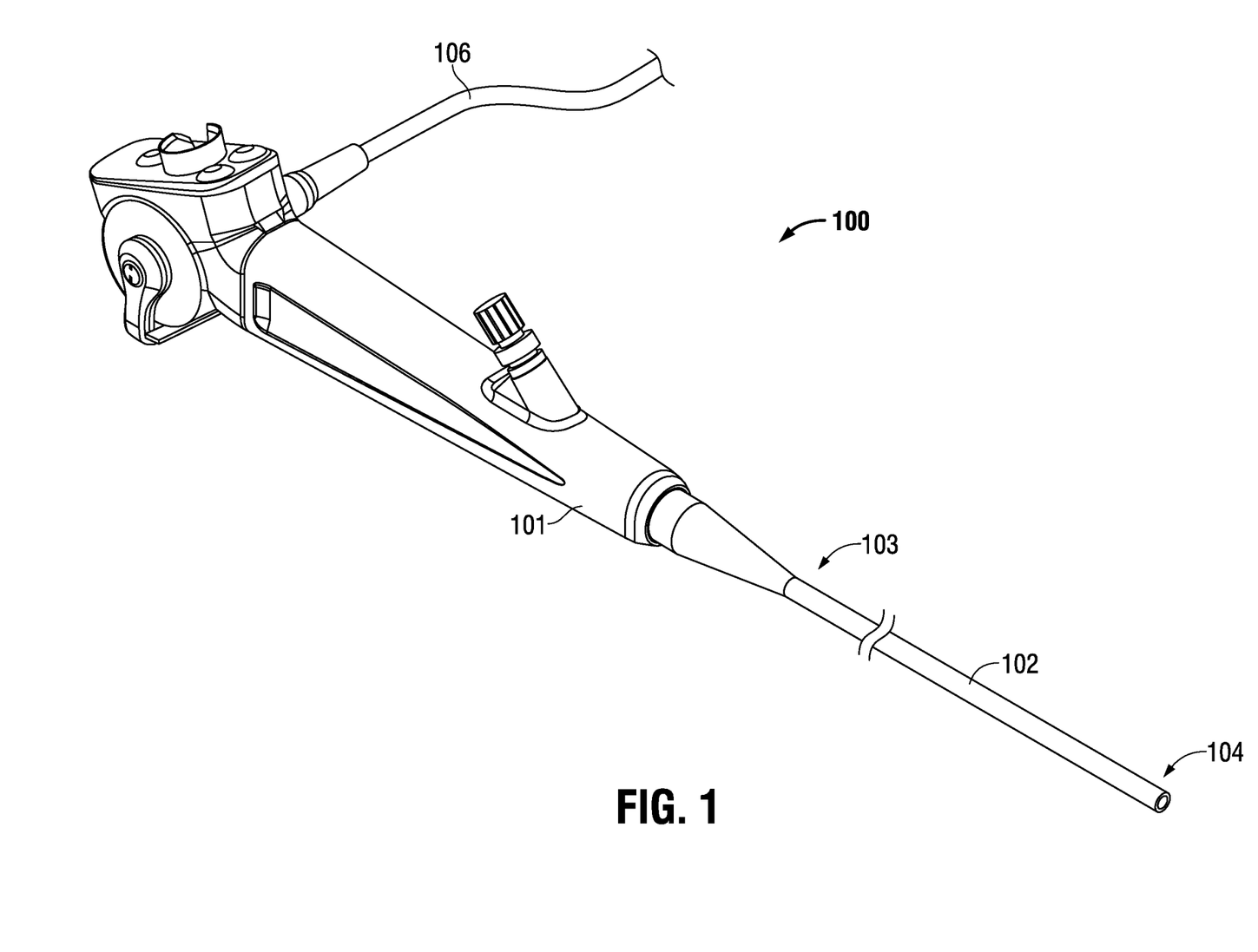
FIG. 1 is a perspective view of an endoscope employing an image sensor module according to an embodiment of the present invention.

Referring to FIG. 1, an endoscope 100 embodying the principles of the invention includes an instrument body 101 and an elongated shaft 102. Elongated shaft 102 includes a proximal end 103 connected to instrument body 101 and a distal end 104. Endoscope 100 also includes a power/communications cable 106 through which power may be supplied to the endoscope. Data and control signals may also be communicated to and from endoscope 100 through wires included in cable 106. Shaft 102 includes an outer sheath that protects and covers internal components which are not visible in FIG. 1. Such internal components include an imaging device located at the shaft distal end 104. The imaging device will be described below in connection with FIG. 2, and an image sensor module included in the imaging device will be described below particularly in connection with FIGS. 3 and 4. Shaft 102 is preferably flexible along as much of its length as possible to facilitate placement of the shaft in a cavity in the course of an endoscopic procedure. As will be described further below, image senor modules according to embodiments of the present invention may provide a compact form particularly along a longitudinal axis of the module. This compact form allows a shaft such as shaft 102 to remain flexible over more of its length.

It should be appreciated that the particular endoscope shown FIG. 1 is shown just for purposes of example and is not intended to limit the types of endoscopes encompassed within the scope of the invention. In particular, although endoscope 100 shown FIG. 1 is particularly adapted for medical use, the invention encompasses endoscopes which may be used for non-medical applications. Furthermore, an endoscope according to the present invention may include additional features not apparent from the example endoscope 100 shown in FIG. 1. For example, an endoscope which may use an image sensor module according to the invention may include tools or instruments located at the shaft distal end which are operated through various controls associated with the endoscope.

Figure 2:
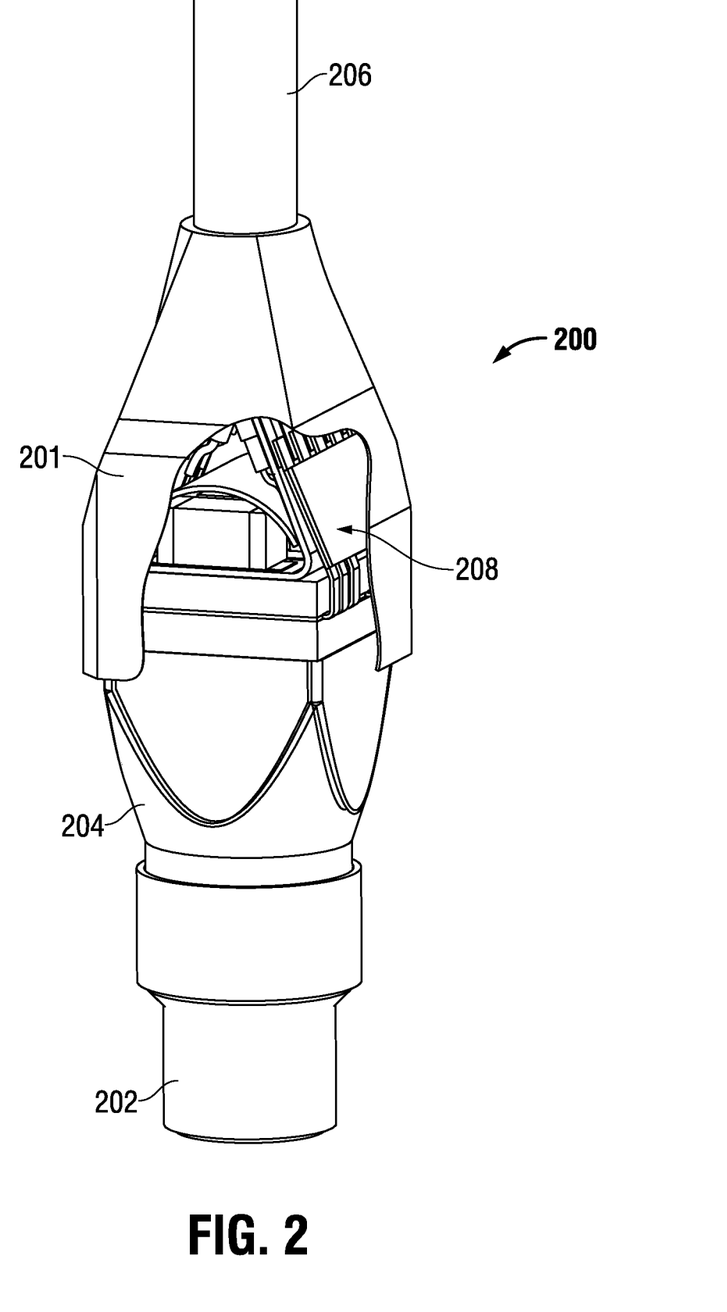
FIG. 2 is a perspective view of an imaging device incorporating an image sensor module according to an embodiment of the present invention, with a module housing for the imaging device being partially broken away to show a portion of the image sensor module.

FIG. 2 shows an imaging device 200 which may be employed in endoscope 100 and which includes an image sensor module according to an embodiment of the present invention. Imaging device 200 includes a module housing 201, a lens assembly 202, and an adapter 204 connected between the module housing and lens assembly. A cable assembly, in this case including a single cable 206, is connected to the end of imaging assembly 200 opposite to the end having lens assembly 202. A portion of module housing 201 is broken away in FIG. 2 to show a portion of image sensor module 208 contained within the module housing.

Lens assembly 202 includes one or more lenses (not shown) to focus and direct light to image sensor module 208. Adapter 204 connects lens assembly 202 to sensor module 208 and provides a conduit through which light travels from the lens assembly to the sensor module. Lens assemblies and the connection of such assemblies to an image sensor module are well known in the art and will not be described further here so as not to obscure the present invention in unnecessary detail.

Figure 3:
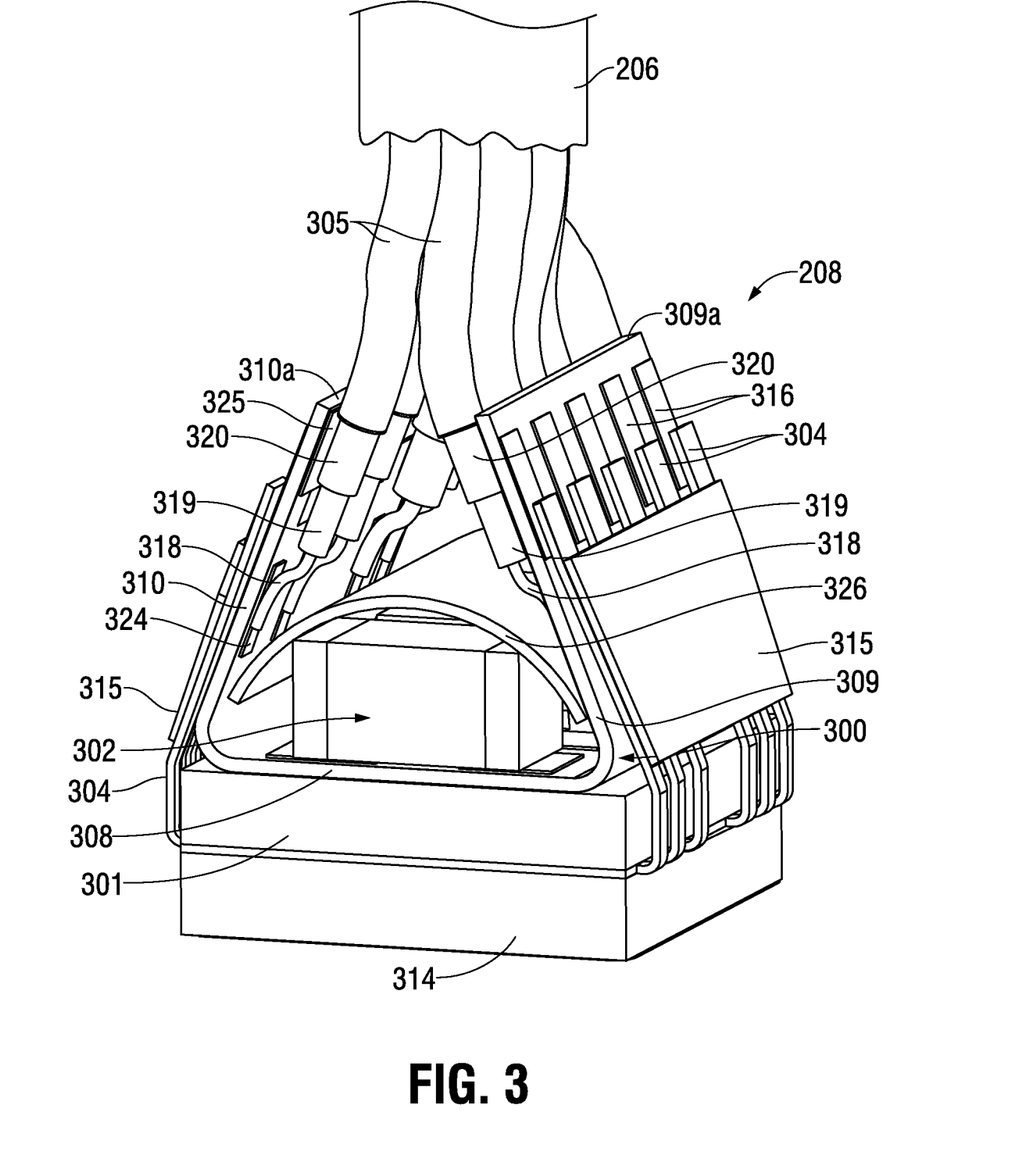
FIG. 3 is a perspective view of the image sensor module shown in FIG. 2.
Figure 4:
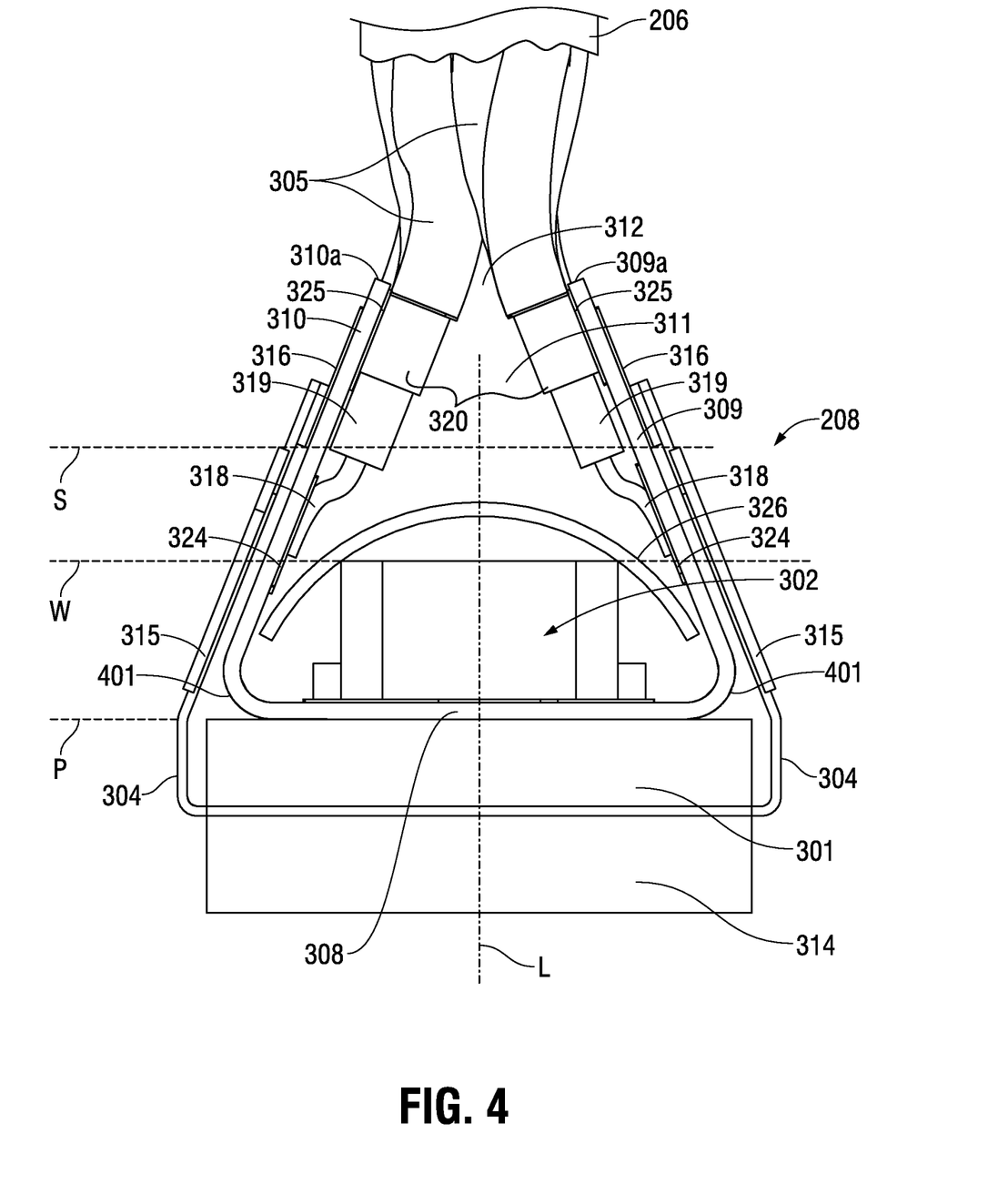
FIG. 4 is a side view of the image sensor module shown in FIG. 3.

FIGS. 3 and 4 show image sensor module 208 with the module housing 201, lens assembly 202, and adapter 204 shown in FIG. 2 removed, and with a portion of the cable sheathing broken away. Image sensor module 208 includes a circuit board 300 on which is mounted an image sensor 301 and an electronic component arrangement 302. Sensor contact fingers 304 extend from lateral sides of image sensor 301 and are operatively connected to circuit board 300, as are cable assembly wires 305.

Circuit board 300 includes a center section 308 located between a first end section 309 and a second end section 310. Image sensor 301 is attached to an outer face of circuit board 300 in center section 308. Electronic component arrangement 302 is operatively connected to an inner face of the circuit board in the center section 308, generally opposite to image sensor 301 mounted on the outer face of the circuit board. Wires 305 from cable assembly 206 are operatively connected at the inner face of circuit board 300 in the end sections 309 and 310. Image sensor contact fingers 304 are operatively connected at the outer face of circuit board 300 in end sections 309 and 310.

As shown in FIG. 4, circuit board center section 308 is aligned with a plane P (defined by the inner face of the circuit board in the center section) lying perpendicular to a longitudinal axis L of image sensor module 208. Both end sections 309 and 310 extend away from plane P of center section 308 to define an interior area of the image sensor module. This interior area is indicated generally at 311 in FIG. 4. An end gap 312 is defined between the distal (outer) edges, 309a and 310a, respectively, of the end sections 309 and 310. As best shown in FIG. 4, this particular embodiment of an image sensor module within the scope of the invention has end sections 309 and 310 which converge in the direction away from circuit board center section 308 so that the planes of the end sections form a triangular shape with the plane P of the center section. Alternative arrangements of circuit board according to the present invention may include end sections (such as sections 309 and 310) which each extend at substantially a 90 degree angle to the plane P of the center section 308.

In order to accommodate the configuration of circuit board 300 shown in FIGS. 3 and 4, the circuit board is flexible at least along a portion of its length from the outer edge 309a of end section 309 to the outer edge 310a of end section 310. In some embodiments, circuit board 300 may be flexible only in interface areas between center section 308 and each end section 309 and 310. Such interface areas are shown generally at reference numeral 401 in FIG. 4. Alternatively, circuit board 300 may be flexible along its entire length from the outer edge of one end section 309 or 310 to the outer edge of the opposite end section.

Image sensor 301 includes a transparent cover 314 over a side facing away from circuit board 300. Although not necessary for an understanding of the present invention and thus not shown in the drawings, it will be appreciated that the side of image sensor 301 facing away from circuit board 300 includes an array of light sensing elements which each respond to incident light to produce a corresponding electrical signal. An image is ultimately produced from the electrical signals provided from the array of light sensing elements. Those skilled in the art of digital imaging will appreciate that the nature of the light sensing elements included in image sensor 301 will depend upon the type of image sensor employed. Some embodiments of the invention may employ a charge coupled device (CCD) as image sensor 301 while other embodiments may employ an active pixel sensor device (CMOS image sensor) as sensor 301. The present invention is not limited to any particular type of image sensor 301 or any particular imaging technology provided the image sensor includes contact fingers such as fingers 304 extending from at least one lateral side of the image sensor. The particular image sensor 301 shown in the figures comprises a CCD tabbed package image sensor.

In the example image sensor 301 shown in FIGS. 3 and 4, a respective group of sensor contact fingers 304 extend from each lateral side of the image sensor. The group of sensor contact fingers 304 from a respective lateral side of image sensor 301 are shown connected together with a relatively rigid dielectric support 315, although other forms of the invention may include no such support. Whether connected together or otherwise, sensor contact fingers 304 extend from the respective lateral side of image sensor 301 along the outer face of the circuit board in the respective end section 309 and 310, and are operatively connected to appropriate elements on the circuit board end sections. In particular, the outer face of circuit board end sections 309 and 310 may include soldering pads 316 (shown in FIG. 3) to which the various sensor contact fingers 304 are operatively connected by soldering. Such soldering pads 316 will be described further below in connection with FIGS. 5 and 6.

Each wire 305 in this illustrated embodiment includes a central conductor 318 surrounded by an interior dielectric sheath 319 and then an annular conductor 320 which is in turn covered by an exterior dielectric sheath which forms the outer surface of the wire. As shown in both FIGS. 3 and 4, cable assembly wires 305 extend through end gap 312 (labeled only in FIG. 4) between circuit board end sections 309 and 310, and are operatively connected to appropriate elements at the inner face of the circuit board end sections 309 and 310. The connection elements shown in this exemplary embodiment include wire soldering pads 324 and shield conductor soldering pads 325. The illustrated image sensor module 208 also includes a dielectric shield 326 positioned to ensure electrical isolation between electronic component arrangement 302 and cable assembly wires 305.

FIG. 4 illustrates how image sensor module 208 provides a compact form along longitudinal axis L and along a plane perpendicular to longitudinal axis L. In particular, the connection of the cable assembly wires 305 at the circuit board inner face in the end sections 309 and 310 together with the connection of sensor contact fingers 304 on the circuit board outer face in the end sections 309 and 310 allows cable assembly wires 305 and sensor contact fingers 304 to overlap along longitudinal axis L. In this arrangement, cable assembly wires 305 may extend to a wire connection point along the longitudinal axis L which is closer to circuit board center section 308 than a sensor connection point along longitudinal axis L for the sensor contact fingers 304. In FIG. 4, the wire connection point along longitudinal axis L is represented by the intersection of line W with the longitudinal axis while the sensor connection point along the longitudinal axis is represented by the intersection of line S with the longitudinal axis.

Figure 5:
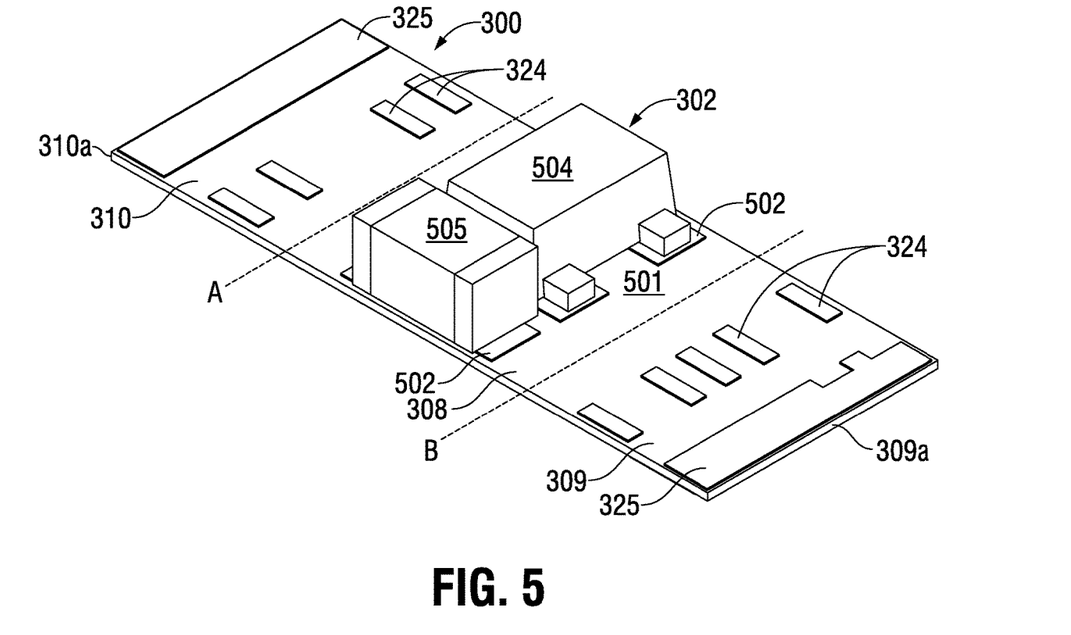
FIG. 5 is a top perspective view of a circuit board which may be employed in an image sensor module according to embodiments of the invention.
Figure 6:
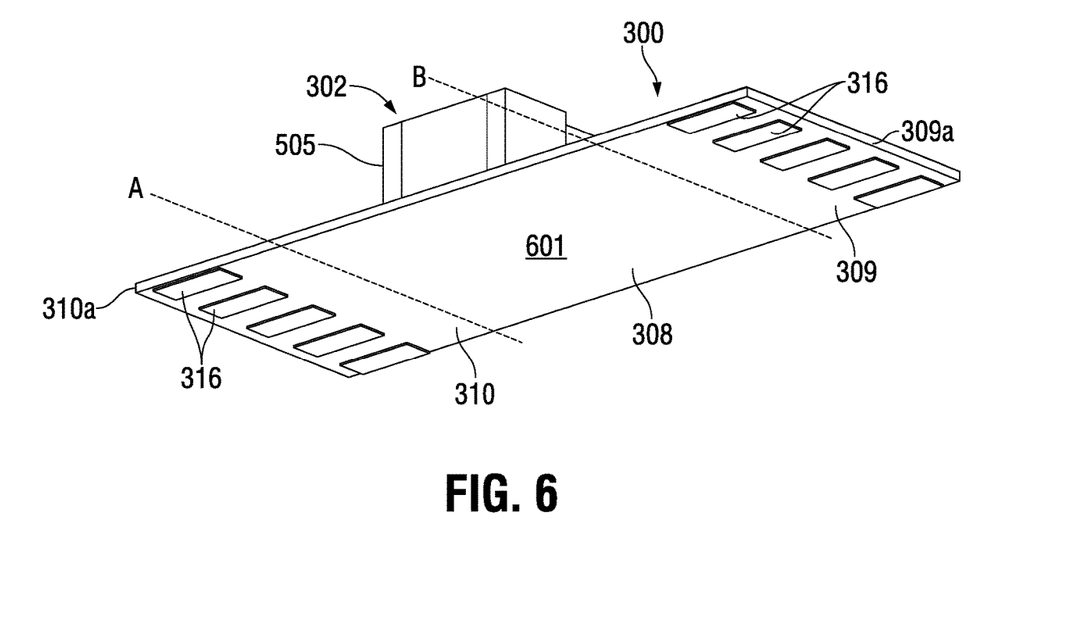
FIG. 6 is a bottom perspective view of the circuit board shown in FIG. 5.

The various components and features of image sensor module 208 and also assembly methods for the image sensor module may be described with reference to FIGS. 5-8 which show various stages of assembly for the image sensor module. Referring first to FIGS. 5 and 6, circuit board 300 may originally be planar and rectangular in shape. Because the illustrated circuit board 300 simply comprises a continuous length of circuit board material, center section 308 and end sections 309 and 310 are not distinguished on the board itself. Therefore FIGS. 5 and 6 (and FIGS. 7 and 8) include dashed lines A and B showing the divisions between center section 308 and end sections 309 and 310. The portion of the end section 309 and 310 adjacent to the respective dashed line A or B can be thought of as the base of the respective end section.

As shown in the perspective of FIG. 5, inner face 501 of circuit board 300 includes soldering pads 502 for connecting electronic component arrangement 302, which in the illustrated case includes a transistor 504 and a capacitor 505. The soldering pad arrangement for the cable assembly wires 305 (the wires themselves shown in FIGS. 3 and 4, but not shown in FIG. 5) are also visible in the perspective of FIG. 5. This soldering pad arrangement includes wire soldering pads 324 for the center conductor (318 in FIGS. 3 and 4) of each wire and a respective common soldering pad 325 for the shield conductors (319 in FIGS. 3 and 4) of each wire to be connected on a given end section 309 or 310.

The perspective of FIG. 6 shows the circuit board outer face 601, which includes sensor finger soldering pads 316. FIG. 6 also shows that outer face 601 in the circuit board center section 308 is left open to provide a surface for attaching image sensor 301.

To produce the desired placement of the sensor contact fingers 304 as shown in FIGS. 3 and 4, sensor finger soldering pads 316 are located in each end section 309 and 310 near the outer edge (309a and 310a) of the respective end section. The desired placement of the cable assembly wires 305 as shown in FIGS. 3 and 4 requires that the wire soldering pads 324 be located on circuit board 300 inwardly of the sensor finger soldering pads 316, toward the center of the circuit board. This relative location of sensor finger soldering pads 316 and wire soldering pads 324 is apparent from FIGS. 5 and 6, and is also shown in FIGS. 7 and 8.

Figure 7:
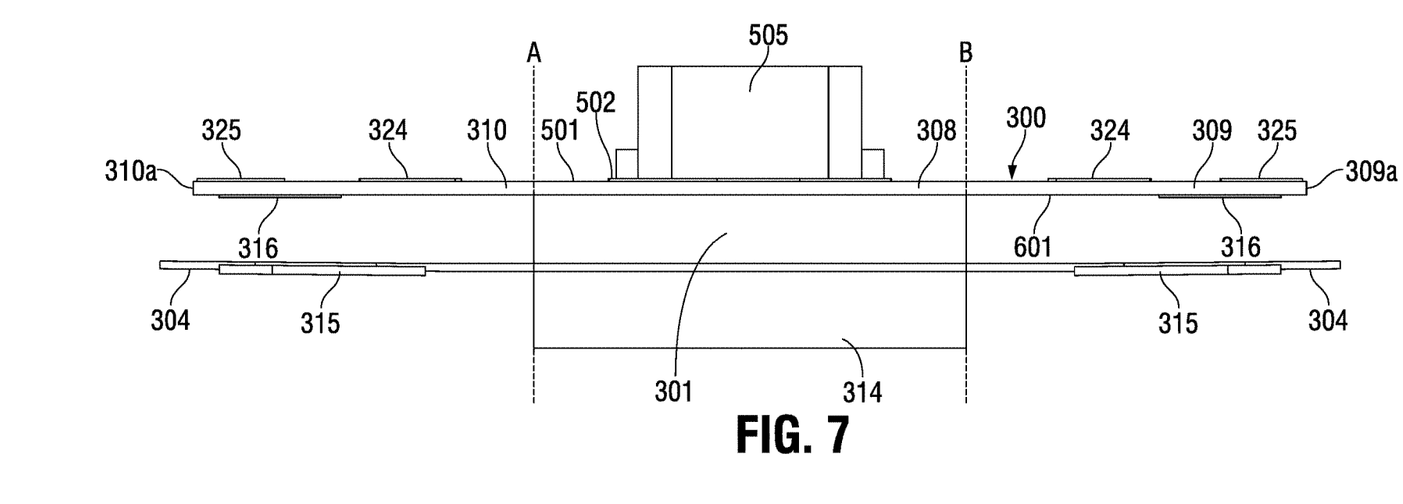
FIG. 7 is a side view of the circuit board shown in FIG. 5 with an image sensor secured thereto.

FIG. 7 shows a point in an assembly process in which image sensor 301 has been attached to circuit board 300. Image sensor 301 may be attached to circuit board outer face 601 using any suitable technique. For example, image sensor 301 may be attached with a suitable bonding agent such as an epoxy adhesive (not shown) applied to circuit board 300 or the image sensor, or both. At the time image sensor 301 is attached to circuit board center section 308, sensor contact fingers 304 extend generally outwardly from the respective lateral side of the image sensor and parallel to the plane of the image sensor. Of course it will be appreciated that sensor contact fingers 304 may be very thin electrical conductors and may flex under their own weight rather than extend rigidly in the position shown in FIG. 7. It should also be noted that the adhesive material may not extend to the lateral sides of image sensor 301 to facilitate separation between the circuit board and image sensor in the bending process described below. This separation is apparent from the side view of FIG. 4.

Figure 8:
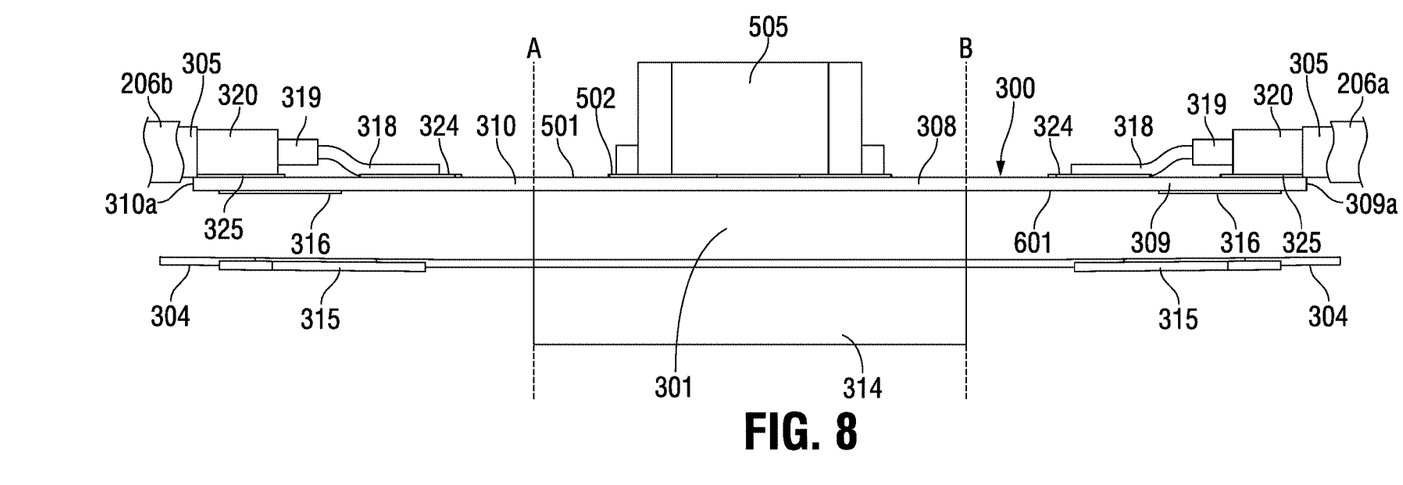
FIG. 8 is a side view similar to FIG. 7, but showing cable assembly wires connected to pads at the inner face of the circuit board.

FIG. 8 shows a point in an assembly process in which cable assembly wires 305 are connected to circuit board 300. In this example, cable assembly wires 305 are soldered to the contact pads (324 and 325) while circuit board 300 remains (is held) in the planar state, and before placing the circuit board in the configuration shown in FIGS. 3 and 4. In order to facilitate soldering cable assembly wires 305, at least the end of each wire is positioned to run generally parallel to the plane of the respective circuit board end section 309 or 310 as shown. In embodiments where cable assembly 206 includes a single cable, this positioning of cable assembly wires 305 may be accomplished by removing or pulling back a portion of the cable assembly sheath at the end of the cable, and separating the cable assembly wires so that the ends of those wires may be placed in the desired orientation shown in FIG. 8. In embodiments where two separate cables are included in cable assembly 206, one cable (206a in FIG. 8) may be placed so that its end runs parallel to the plane of circuit board 300 and the associated wires 305 can be connected at the respective end section 309 or 310. The second cable (206b in FIG. 8) may be positioned in the same way relative to the opposite end section 309 or 310 so that its wires may be connected to the pads at that end section.

From the position shown in FIG. 8, circuit board 300 may be bent (upwardly in the orientation of FIG. 8) in each area at which center section 308 meets a respective end section 309 and 310, generally with the center of curvature at the points at which lines A and B intersect the circuit board (corresponding to the areas 401 in FIG. 4) to place the circuit board in the desired orientation with end sections 309 and 310 extending away from the plane P of the center section as shown in FIG. 3. Although end sections 309 and 310 may be bent to only approximately 90 degrees with respect to the plane of center section 308, this bending step may include bending each end section 309 and 310 through an angle greater than 90 degrees so that the end sections converge as shown in FIGS. 3 and 4. In any case, end sections 309 and 310 are left in a position defining end gap 312 (shown in FIG. 4) which allows cable assembly wires 305 to extend into the interior space defined between end sections 309 and 310 and center section 308. Also, because cable assembly wires 305 are preferably already soldered to circuit board 300 at the time the circuit board 300 is bent to the desired arrangement, cable assembly wires 305 must also be repositioned and perhaps bent as necessary concurrently with bending the circuit board.

Once circuit board end sections 309 and 310 are placed in the desired orientation relative to center section 308, and cable assembly wires 305 are repositioned appropriately, sensor contact fingers 304 may be bent so as to place the ends of the sensor contact fingers in position to be soldered to the respective pad 316 on the circuit board outer face 601. After sensor contact fingers 304 are all soldered appropriately, a module housing (such as housing 201 shown in FIG. 2) may be connected over completed image sensor module 208. An adapter and lens assembly (such as adapted 204 and lens assembly 202 in FIG. 2) may then be connected to the module housing to complete the imaging assembly. The completed imaging assembly may then be incorporated into an endoscope such as endoscope 100 shown in FIG. 1.

Assembly methods according to the present invention include a number of variations from the general process steps described above in connection with FIGS. 5-8. For example, although FIGS. 5 and 6 show circuit board 300 already populated with electronic component arrangement 302, an assembly method within the scope of the present invention may start with a completely unpopulated circuit board 300 and include operatively connecting the electronic component arrangement 302 or at least some part of that arrangement. Where an assembly method includes connecting the electronic component arrangement 302 and image sensor 301, these components may be connected in any order. Similarly, cable assembly wires 305 may be soldered to the soldering pads 324 and 325 in any order relative to connecting electronic component arrangement 302 and image sensor 301. Sensor contact fingers 304 are preferably soldered to soldering pads 316 after circuit board 300 is bent to the configuration shown in FIGS. 3 and 4. However, it is possible to solder the sensor contact fingers 304 in place prior to bending circuit board 300 if sufficient slack is left in the sensor contact fingers or the sensor contact fingers are otherwise capable of accommodating bending to follow the circuit board from its planar state to the final configuration shown in FIGS. 3 and 4.

Also, it will be appreciated by those familiar with circuit boards that circuit board 300 may include internal conduction paths and vias to interconnect the soldering pads to provide an operative circuit. The specific connection from, for example, one of the sensor soldering pads 316 to one of the electronic component pads 502 or cable assembly wire pads 324, is not relevant to the present invention, and is thus not disclosed herein. The various soldering pads comprise layers of conductive material which may be deposited or attached to the circuit board base material and thus may protrude slightly from the circuit board base material as shown particularly in FIGS. 7 and 8. Although these soldering pads protrude slightly from the circuit board base material they remain part of the circuit board and define part of the respective face of the circuit board as the term "face" is used in this disclosure and the following claims.

The various components of an image sensor module according to the present invention may be formed from any suitable material or combination of materials. For example, circuit board 300 may be formed from a base material comprising a suitable flexible polymer such as a polyimide film to provide the desired flexibility described above. The circuit board may be less than 0.1 mm in thickness to accommodate the desired bending. Module housing 201 may be formed from a suitable thermoplastic, as may the adapter 204 and housing for the lens assembly 202. Although a molded module housing 201 is shown in FIG. 2 for purposes of example, the module housing may be formed from a heat shrink material in other embodiments. Also, the interior area between circuit board end sections 309 and 310 may or may not be filled with a suitable potting material.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having the same name (but for use of the ordinal term).

In the above descriptions and the following claims, terms such as top, bottom, outer, inner, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. An image sensor module comprising:
   (a) a circuit board defining an outer face and an inner face, and including a center section located between a first end section and a second end section, the first end section and second end section each extending away from the center section to define an interior area there between which terminates in an end gap between the first end section and second end section;
   (b) an image sensor secured to the outer face in the center section, the image sensor having a number of contact fingers extending from the image sensor along the outer face in the first end section at least to a contact finger connection point;
   (c) an electronic component arrangement operatively mounted on the inner face in the center section; and
   (d) a cable assembly including a number of wires extending through the end gap, the wires being operatively connected to the inner face with at least one of the wires being connected to the inner face at a wire connection point which is closer than the contact finger connection point to a plane defined by the inner face in the center section.

2. The image sensor module of claim 1 wherein the first end section and second end section converge in a direction away from the center section.

3. The image sensor module of claim 1 wherein the circuit board is flexible in a first interface area between the first end section and center section and is flexible in a second interface area between the second end section and center section.

4. The image sensor module of claim 1 wherein the circuit board is flexible along the entire length and width thereof.

5. The image sensor module of claim 1 wherein a first portion of the wires are connected in the first end section and a second portion of the wires are connected in the second end section.

6. The image sensor module of claim 5 wherein the first portion of the wires are included in a first cable and the second portion of the wires are included in a second cable separate from the first cable.

7. The image sensor module of claim 1 further including a dielectric shield separate from the electrical component arrangement, the dielectric shield separating the electric component arrangement from the wires operatively connected to the inner face.

8. An endoscope comprising:
   (a) an instrument body;
   (b) an elongated shaft having a proximal end operatively connected to the instrument body with one or more cables extending through the elongated shaft to an interior of the instrument body;
   (c) an imaging assembly mounted at a distal end of the elongated shaft; and
   (d) an image sensor module included in the imaging assembly, the image sensor module including:
      (i) a circuit board defining an outer face and an inner face, and including a center section located between a first end section and a second end section, the first end section and second end section each extending away from the center section to define an interior area there between which terminates in an end gap between the first end section and second end section;
      (ii) an image sensor secured to the outer face in the center section, the image sensor having a number of contact fingers extending from a first lateral side of the image sensor along the outer face in the first end section at least to a contact finger connection point;
      (iii) an electronic component arrangement operatively mounted on the inner face in the center section; and
      (iv) a cable assembly including a number of wires from the one or more cables extending through the shaft, the number of wires extending through the end gap and being operatively connected to the inner face with at least one of the wires being connected to the inner face at a wire connection point which is closer than the contact finger connection point to a plane defined by the inner face in the center section.

9. The endoscope of claim 8 wherein the first end section and second end section converge in a direction away from the center section.

10. The endoscope of claim 8 wherein the circuit board is flexible in a first interface area between the first end section and center section and is flexible in a second interface area between the second end section and center section.

11. The endoscope of claim 8 wherein the circuit board is flexible along the entire length and width thereof.

12. The endoscope of claim 8 wherein a first portion of the wires are connected in the first end section and a second portion of the wires are connected in the second end section.

13. The endoscope of claim 12 wherein the first portion of the wires are included in a first cable and the second portion of the wires are included in a second cable separate from the first cable.

14. The endoscope of claim 8 further including a dielectric shield separate from the electrical component arrangement, the dielectric shield separating the electric component arrangement from the wires operatively connected to the inner face.

15. A method of assembling an image sensor module, the method comprising:
   (a) attaching an image sensor to an outer face of a planar circuit board in a center section of the circuit board, the circuit board defining an inner face comprising a surface opposite to the outer face, and the center section being located between a first end section and a second end section of the circuit board, the image sensor being attached to the circuit board so that a number of contact fingers extend from a first lateral side of the image sensor at a base of the first end section;
   (b) soldering each of a number of wires of a cable assembly to a respective set of one or more wire soldering pads located on the inner face;
   (c) bending the circuit board so that the first end section and the second end section are brought toward each other to an assembled position in which the inner face in the first end section and the inner face in the second end section each extend away from the center section;
   (d) after or concurrently with bending the circuit board so that the first end section and second end section are brought toward each other to the assembled position, bending the number of contact fingers toward the outer face in the first end section; and
   (e) after bending the circuit board, soldering the number of contact fingers to respective sensor soldering pads located on the outer face in the first end section so that at least one of the contact fingers extends to a point spaced further than at least one of the number of the wire soldering pads from a plane defined by the inner face in the center section.

16. The method of claim 15 wherein the circuit board is flexible in a first interface area between the first end section and center section and is flexible in a second interface area between the second end section and center section.

17. The method of claim 15 wherein the circuit board is flexible along the entire length thereof from an outer edge of the first end section to an outer edge of the second end section.

18. The method of claim 15 wherein soldering each of the number of wires includes soldering each of a first portion of the wires to wire soldering pads in the first end section and soldering each of a second portion of the wires to wire soldering pads in the second end section.

19. The method of claim 18 wherein the first portion of the wires are included in a first cable and the second portion of the wires are included in a second cable separate from the first cable, and further including repositioning the first cable and second cable as the circuit board is bent.

20. The method of claim 15 wherein an electronic component arrangement is operatively connected on the inner face of the circuit board in the center section, and further including connecting a dielectric shield over at least a portion of the electronic component arrangement so as to separate that portion of the electronic component arrangement from the wires when the circuit board is bent to the assembled position.

* * * * *